United States Patent [19]

Zeitoun et al.

[11] 4,432,966
[45] Feb. 21, 1984

[54] COMPRESSED TABLETS FOR DISINTEGRATION IN THE COLON COMPRISING AN ACTIVE INGREDIENT CONTAINING NUCLEUS COATED WITH A FIRST LAYER CONTAINING MICROCRYSTALLINE CELLULOSE WHICH IS COATED WITH AN ENTERIC ORGANIC POLYMER COATING

[75] Inventors: Paul Zeitoun, Reims; Patrick Brisard, Paris, both of France

[73] Assignee: Roussel-UCLAF, Romainville, France

[21] Appl. No.: 413,483

[22] Filed: Aug. 31, 1982

Related U.S. Application Data

[63] Continuation of Ser. No. 214,413, Dec. 8, 1980, abandoned.

[30] Foreign Application Priority Data

Dec. 8, 1980 [FR] France .............................. 79 30202

[51] Int. Cl.$^3$ .......................... A61K 9/24; A61K 9/36
[52] U.S. Cl. .......................................... 424/21; 424/35
[58] Field of Search ...................... 424/19–22, 424/35; 106/163; 536/56

[56] References Cited

U.S. PATENT DOCUMENTS

| | | | |
|---|---|---|---|
| 2,687,367 | 8/1954 | Burrin .............................. | 424/35 |
| 2,798,024 | 7/1957 | Zapapas et al. .................. | 424/35 |
| 2,853,420 | 9/1958 | Lowey ............................. | 424/35 |
| 2,928,770 | 3/1960 | Bardani ........................... | 424/21 |
| 2,991,226 | 7/1961 | Millar et al. .................... | 424/21 |
| 3,143,472 | 8/1964 | Lappas et al. ................... | 424/33 |
| 3,162,541 | 12/1964 | Battista ........................... | 106/165 |
| 3,192,118 | 6/1965 | Battista et al. .................. | 424/4 |
| 3,258,354 | 6/1966 | Battista ........................... | 106/163 |
| 3,259,537 | 7/1966 | Battista ........................... | 536/56 X |
| 3,278,519 | 10/1966 | Battista et al. .................. | 536/56 |
| 3,357,845 | 12/1967 | Battista ........................... | 536/56 X |
| 3,371,015 | 2/1968 | Sjogren et al. .................. | 424/33 |
| 3,372,132 | 3/1968 | Cruz ............................... | 536/56 X |
| 3,420,931 | 1/1969 | Daum et al. ..................... | 424/33 |
| 3,431,338 | 3/1969 | Munzel ............................ | 424/21 |
| 3,784,683 | 1/1974 | Prillig et al. .................... | 424/35 |
| 3,957,523 | 5/1976 | Ohno et al. ...................... | 424/362 |
| 3,981,984 | 9/1976 | Signorino ........................ | 424/35 |
| 4,001,390 | 1/1977 | Ohno et al. ...................... | 424/35 |
| 4,193,985 | 3/1980 | Bechgaard ....................... | 424/4 |
| 4,274,830 | 6/1981 | Woznicki et al. ................. | 424/35 |

FOREIGN PATENT DOCUMENTS

| | | | |
|---|---|---|---|
| 40-26918 | 11/1965 | Japan ............................... | 424/35 |
| 41-10839 | 6/1966 | Japan ............................... | 424/35 |
| 42-25410 | 12/1967 | Japan ............................... | 424/4 |
| 42-25412 | 12/1967 | Japan ............................... | 424/4 |
| 44-10799 | 5/1969 | Japan ............................... | 424/4 |
| 44-10798 | 5/1969 | Japan ............................... | 424/4 |
| 44-27839 | 11/1969 | Japan ............................... | 424/4 |
| 45-5275 | 2/1970 | Japan ............................... | 424/19 |
| 45-5277 | 2/1970 | Japan ............................... | 424/20 |
| 46-2117 | 1/1971 | Japan ............................... | 424/21 |
| 48-24246 | 7/1973 | Japan ............................... | 424/4 |
| 1538123 | 1/1979 | United Kingdom . | |

*Primary Examiner*—Shep K. Rose
*Attorney, Agent, or Firm*—Bacon & Thomas

[57] ABSTRACT

Coated compressed tablets for oral administration are disclosed which substantially desintegrate specifically at the level of the colon. The tablets comprise a compressed center piece containing an active agent which center piece is coated by a first coating layer which is comprised of a mixture of a pharmaceutically acceptable film-forming organic polymer material which is non-deteriorated by a neutral or alkaline aqueous medium and microcrystalline cellulose and a second coating layer which is comprised of a pharmaceutically acceptable enteric organic polymer coating material.

7 Claims, No Drawings

COMPRESSED TABLETS FOR DISINTEGRATION IN THE COLON COMPRISING AN ACTIVE INGREDIENT CONTAINING NUCLEUS COATED WITH A FIRST LAYER CONTAINING MICROCRYSTALLINE CELLULOSE WHICH IS COATED WITH AN ENTERIC ORGANIC POLYMER COATING

This application is a continuation of application Ser. No. 214,413, filed Dec. 8, 1980, now abandoned.

BACKGROUND OF THE INVENTION

The present invention relates to new compressed tablets for disintegration in the colon, as well as a process for preparing same.

In the present specification and claims the term "compressed tablets for disintegration in the colon" is meant to connote compressed tablets of which the center containing the active agent is substantially disintegrated specifically at the level of the colon.

From the French Patent No. 1,591,602 there are known pharmaceutical compositions in unit dosage forms for oral administration, in which the active agents remain substantially protected from the digestive juices of the stomach and of the small intestine, and are practically entirely released in the colon. In these pharmaceutical dosage forms the pharmacologically active agents are finely divided and coated by a resin.

These dosage forms possess a certain number of disadvantages. The duration of the gastro-intestinal passage varies considerably from one individual to another and depending on the size of the meals this individual has consumed it can range from about twelve hours to more than twenty-four hours. Given that the degree of dissolution of resin covering the active agents is proportional to the passage time, release of the pharmacologically active ingredients exactly at the level of the colon is rather uncertain. In addition, it is difficult to coat the active agents homogeneously.

Attempts have, therefore, been made to find a technique other than simple dissolution in order to achieve complete specificity of release of the active agents at the level of the colon.

SUMMARY OF THE INVENTION

It is an object of the present invention to provide novel pharmaceutical formulation of active agents which is in the form of a coated tablet for disintegration in the colon, and which avoids the drawback of prior art compositions and wherein substantially complete disintegration of the center portion including the active agents and substantially complete release of the active agents specifically at the level of the colon is secured independently from the passage time of the tablet through the gastrointestinal tract.

In order to achieve this object there is provided a novel compressed pharmaceutical formulation of a pharmacologically active agent for oral administration and release of this active agent in the colon which is a coated tablet for disintegration in the colon which is characterized in that it is constituted by a solid center piece, e.g. a tablet containing the active agent, optionally in admixture with pharmaceutically acceptable carriers and additives, covered successively: with a first coating layer composed of a pharmaceutically acceptable film-forming organic polymer material which does not deteriorate in a neutral or alkaline medium and of microcrystalline cellulose and with a second coating layer composed of an enteric coating material.

DETAILED DESCRIPTION OF THE INVENTION

It is known that the digestive tract of man is devoid of specific enzymes permitting the digestion of cellulose; on the other hand, bacteria existing at the level of the human colon have the ability to digest cellulose.

The novel compressed tablets of the present invention comprise as a center a compressed tablet containing the active agent, optionally in admixture with conventional pharmaceutical diluents and additives, e.g. tabletting aids, wetting agents and coloring agents. Suitable carrier materials and additives are known from standard handbooks, for example from "Remington's Pharmaceutical Sciences", 13th edition, or "Hagers Handbuch der Pharmazeutischen Praxis", 4th edition. The amount of carriers and/or additives in the center tablet will vary depending on the desired dosage per tablet of the active agent and/or its tabletting behavior.

This center tablet is covered by two different coating layers. The first of these layers is comprised of microcrystalline cellulose and a pharmaceutically acceptable film-forming organic polymer material which is non-deteriorated by neutral or alkaline aqueous solutions.

The microcrystalline cellulose is, for example, that sold under the name of Rehocel (Rettenmaier), Avicel PH (American Viscose Division), Avicel RC (Lehmann and Voss) or Lintenspuver LH 330 (Rettenmaier).

The film-forming polymer material can be chosen amonst any such pharmaceutically acceptable film-forming polymers which do not deteriorate in contact with a neutral or alkaline aqueous medium. Suitable such film-forming materials include lower alkyl ethers of cellulose. Ethyl cellulose is particularly preferred.

Conventional enteric coating materials are suitable for forming the second coating layer. Suitable enteric coating materials are known, for example, from "Remington's Pharmaceutical Sciences", 13th edition, pages 601 to 605 and "Hagers Handbuch der Pharmazeutischen Praxis", 4th edition, volume 7a (Springer Verlag 1971), pages 739 to 742 and 776 to 778 which are included herein by reference.

Examples of suitable enteric coating materials include cellulose acetylphthalate, hydroxypropylmethylcellulose phathalate, benzophenyl salicylate, cellulose acetosuccinate, copolymers of styrene and of maleic acid, formylated gelatin, salol, keratin, stearic acid, myristic acid, gluten, acrylic and methacrylic resins, and copolymers of maleic acid and phthalic acid derivatives.

Among the enteric coating materials capable of being contained in the second coating layer, esters of cellulose and hydroxy lower alkyl cellulose, in particular cellulose acetyl phthalate, are considered to be particularly suitable.

In order to have sufficiently fine and solid coating films, the coating layers can contain advantageously, in addition, one or more plasticizers. The plasticizers can be, for example, diethyl phthalate, dibutyl phthalate, propylene glycol or castor oil or mixtures thereof.

The plasticizers are preferably selected from the group consisting of diethyl phthalate, dibutyl phthalate and propylene glycol and mixtures thereof.

Among the compressed tablets which form the subject of the invention there are considered especially those wherein the amount of the first coating layer is between about 0.5% and about 10% by weight of that of the center, and in that said amount of the first coating layer comprises from about 30% to about 80% by weight of microcrystalline cellulose.

Among the compressed tablets according to the invention there are also considered especially those wherein the amount of enteric coating materials is between about 2% and about 10% by weight of that of the center.

It is evident to anyone skilled in the art the coating layers of the tablets of the present invention may further contain conventional adjuvants, for example, coloring agents or substances capable of protecting the pharmacologically active agents against light. Such adjuvants for coatings are well known, for example, from the above cited pharmaceutical handbooks.

According to the present invention there is further provided a process for preparing the above described novel double-coated tablets which comprises the steps of (a) applying to tablets containing an active agent a first coating layer by spraying the tablets with a solution of a pharmaceutically acceptable film-forming organic polymer material which is non deteriorated by a neutral or alkaline aqueous medium containing microcrystalline cellulose and which, if desired, may contain one or more plasticizers in a solvent or mixture of solvents and subsequently drying the sprayed tablets to obtain a coated tablet, and (b) applying to the coated tablets a second coating layer by spraying the coated tablets with a solution of a pharmaceutically acceptable enteric organic polymer coating material which, if desired, may contain one or more plasticizers in a solvent or mixture of solvents and subsequently drying the sprayed coated tablets.

The compressed tablets containing the active agents which form the center piece of the double coated tablets of the present invention are prepared by conventional tabletting methods, for example, such as are described in the above cited pharmaceutical handbooks.

The spraying solutions are prepared in conventional manner by dissolving the respective polymers and optionally plasticizers in a suitable solvent or mixture of solvents, for example in a lower alkyl alcohol such as methanol, ethanol or isopropanol, in acetone, ethylacetate, ethylene chloride or in mixtures of these solvents. For preparing the first spraying solution the microcrystalline cellulose is incorporated into the solution of the film-forming polymer. The coating can be carried out by spraying the tablets into a tumbler or whilst they are held in suspension in the air. The tumbler method is preferred.

The double coated tablets of the present invention provide the effect of delayed release of the active agent, and a local effect at the level of the colon. Because of these effects, the double coated tablets of the present invention are particularly useful for achieving a delayed action for pharmacologically active agents such as barbiturates, amphetamine or aspirin.

Furthermore, a local effect of a pharmacologically active agent at the level of the colon also is often desired for example in the treatment of certain parasitic infections such as colic amoebiases.

Among the pharmacologically active agents which can advantageously be formulated and orally administered in form of the compressed tablets of the present invention, there are considered in particular active agents for which a delayed effect and/or a local effect are desired, such as corticoids, antiinflammatory agents, antibacterial agents or antibiotics.

The following non-limiting examples are given in order to further demonstrate the carrying out of the invention:

EXAMPLE 1

Preparation of Neomycin Compressed Tablets

500 Compressed tablets of 400 mg weight containing 200 mg of neomycin sulphate are introduced into a glass tumbler rotating at 30 revolutions/minute, and sprayed for a period of 40 minutes, under a pressure of 0.3 bar, at ambient temperature, with 22.5 ml of a solution of ethyl cellulose composed of:

| | |
|---|---|
| ethyl cellulose | 60 g |
| dibutylphthalate | 25 g |
| propylene glycol | 15 g |
| isopropanol | 650 ml |
| ethanol | 650 ml |
| into which microcrystalline cellulose (Avicel PH 101) had been incorporated. | 1.25 g |

The sprayed tablets are left to dry for one night under vacuum, 500 coated center pieces having an average weight of 403 mg are thus obtained, these are subsequently sprayed, for a period of one hour, under a pressure of 0.1 bar, at ambient temperature, with 320 ml of a solution composed of:

| | |
|---|---|
| cellulose acetylphthalate | 50 g |
| diethylphthalate | 5 g |
| isopropanol | 500 ml |
| ethyl acetate | 500 ml |

The sprayed tablets are left again for one night under vacuum and 500 coated compressed tablets are obtained, having an average weight of 428 mg.

EXAMPLE 2

Preparation of Prednisolone Compressed Tablets

500 Tablets of 398 mg weight containing 5 mg of prednisolone are introduced into a glass tumbler, rotating at 40 revolutions/minute, and sprayed over a period of 35 minutes, under a pressure of 0.2 bar, at ambient temperature, with 45 ml of a solution of ethyl cellulose composed of:

| | |
|---|---|
| ethyl cellulose | 60 g |
| dibutylphthalate | 25 g |
| propylene glycol | 15 g |
| isopropanol | 650 ml |
| ethanol | 650 ml |
| into which microcrystalline cellulose (Avicel PH 101) had been incorporated. | 5 g |

45 ml of a mixture of equal amounts of isopropanol and ethyl alcohol were added, partial drying was carried out in fresh air, and the tablets are left to dry for one night under vacuum. 500 coated center pieces are thus obtained, having an average weight of 411 mg. These were subsequently sprayed for a period of one and a half hours, at ambient temperature, under a pressure of 0.1 bar, and under constant drying with fresh air, with 320 ml of a solution composed of:

| | |
|---|---|
| cellulose acetylphthalate | 50 g |
| diethylphthalate | 5 g |
| isopropanol | 500 ml |
| ethyl acetate | 500 ml |

The sprayed tablets are left again to dry for one night under vacuum, 500 coated compressed tablets are obtained, having an average weight of 444 mg.

EXAMPLES 3, 4, 5, 6, 7

Preparation of Barium Sulphate Compressed Tablets

Double coated tablets are prepared according to the process described in Example 2, the center pieces have an average weight of 398 mg and contain 100 mg of barium sulphate.

| | EXAMPLES | | | | |
|---|---|---|---|---|---|
| | 3 | 4 | 5 | 6 | 7 |
| Ethyl cellulose solution | 29.8 ml | 34.2 ml | 37.0 ml | 40.3 ml | 44.2 ml |
| Microcrystalline cellulose | 2.72 g | 2.87 g | 2.90 g | 3 g | 3 g |
| Isopropanol/ethanol mixture | 29.8 ml | 34.2 ml | 37.0 ml | 40.3 ml | 44.2 ml |
| Final weight of the compressed tablet | 444 mg | 438 mg | 438 mg | 440 mg | 434 mg |

CLINICAL STUDY (A) Study protocol.

The disintegration of the compressed tablets of Examples 3, 4, 5, 6 and 7 was tested, in man. The compressed tablets contain barium sulphate. They are thus visible on a radiographic control.

With dinner (at 7:30 p.m.) and the next day with breakfast (at 7:00-8:00 a.m.) a compressed tablet was given to the patient, that is 2 in all.

A radiograph of the abdomen was taken at between 2:00 and 3:00 p.m., that is about 19 and 7 hours, respectively after the oral dose.

It was possible to observe:

1. The state of disintegration of the compressed tablets which is expressed in the following manner:

intact for a compressed tablet of preserved outline and density, eaten away for a compressed tablet slightly changed in its density and outline, emptied for a compressed tablet of which only the still-locatable shell is visible and disintegrated for a non-visible compressed tablet.

Since none of the patients had motor diarrhoea, the invisible compressed tablets were in reality disintegrated and not removed in the stools.

2. The location of the compressed tablets defines the organ in which they are visible: three were located in the stomach and several in the small or in the large intestine.

(B) Results.

They are given in the summary of observations appearing hereinafter.

The following conclusions can be drawn:

(a) The compressed tablets given the day before in the evening, that is to say 19 hours before the radiograph are always disintegrated;

(b) the compressed tablets which are in the small intestine are always intact;

(c) the compressed tablets which are seen in the colon are rarely intact.

| OBSERVATIONS | | | |
|---|---|---|---|
| FIRST COMPRESSED TABLET Condition and location | | SECOND COMPRESSED TABLET Condition and location | |
| Compressed tablets of Example 3 | | | |
| ADD | DISINTEGRATED | INTACT | CAECUM |
| FRE | DISINTEGRATED | INTACT | RIGHT CORNER OF THE COLON |
| DEL | DISINTEGRATED | DISINTEGRATED | |
| COU | DISINTEGRATED | DISINTEGRATED | |
| KUN | DISINTEGRATED | DISINTEGRATED | |
| MAS | DISINTEGRATED | DISINTEGRATED | |
| KUL | DISINTEGRATED | DISINTEGRATED | |
| SAR | DISINTEGRATED | INTACT | STOMACH |
| BRU | DISINTEGRATED | INTACT | RIGHT CORNER OF THE COLON |
| Compressed tablets of Example 4 | | | |
| KER | DISINTEGRATED | DISINTEGRATED | |
| GOD | DISINTEGRATED | DISINTEGRATED | |
| HUR | DISINTEGRATED | DISINTEGRATED | |
| RYL | DISINTEGRATED | DISINTEGRATED | |
| DIR | DISINTEGRATED | INTACT | SMALL INTESTINE |
| ROY | DISINTEGRATED | INTACT | SMALL INTESTINE |
| BOU | DISINTEGRATED | INTACT | SMALL INTESTINE |
| NGU | DISINTEGRATED | DISINTEGRATED | |
| FEH | EMPTIED CAECUM | INTACT | SMALL INTESTINE |
| Compressed tablets of Example 5 | | | |
| CAM | DISINTEGRATED | DISINTEGRATED | |
| LAM | DISINTEGRATED | DISINTEGRATED | |
| KOC | DISINTEGRATED | INTACT | RIGHT CORNER OF THE COLON |
| LOU | DISINTEGRATED | INTACT | CAECUM |
| SAL | DISINTEGRATED | INTACT | RIGHT CORNER OF THE COLON |
| LAS | DISINTEGRATED | INTACT | RIGHT CORNER OF THE COLON |
| PON | DISINTEGRATED | DISINTEGRATED | |

-continued

| | OBSERVATIONS | | |
|---|---|---|---|
| | FIRST COMPRESSED TABLET Condition and location | | SECOND COMPRESSED TABLET Condition and location |
| | Compressed tablets of Example 6 | | |
| DUR | CAECUM EATEN AWAY | INTACT | SMALL INTESTINE |
| CHA | DISINTEGRATED | INTACT | SMALL INTESTINE |
| DEL | DISINTEGRATED | INTACT | SMALL INTESTINE |
| AIR | DISINTEGRATED | DISINTEGRATED | |
| DER | EMPTIED RIGHT CORNER OF THE COLON | INTACT | SMALL INTESTINE |
| HUR | DISINTEGRATED | DISINTEGRATED | |
| BEN | EMPTIED RIGHT CORNER | INTACT | SMALL INTESTINE |
| | Compressed tablets of Example 7 | | |
| MER | DISINTEGRATED | EATEN AWAY | SMALL INTESTINE |
| FRA | DISINTEGRATED | DISINTEGRATED | |
| BER | DISINTEGRATED | INTACT | SMALL INTESTINE |
| REM | DISINTEGRATED | INTACT | STOMACH |
| GON | DISINTEGRATED | INTACT | RIGHT CORNER |
| JOE | DISINTEGRATED | INTACT | STOMACH |
| NEP | EMPTIED RIGHT CORNER OF THE COLON | INTACT | CAECUM |
| LEG | DISINTEGRATED | DISINTEGRATED | |
| GAU | DISINTEGRATED | DISINTEGRATED | |

What is claimed is:

1. A compressed tablet for oral administration and disintegration in the colon which consists essentially of:
   (a) a microcrystalline cellulose-free compressed center piece containing an active agent;
   (b) a first coating layer amounting to between about 0.5% and about 10% by weight of that of the center, coating the compressed center piece and consisting essentially of a mixture of a pharmaceutically acceptable lower alkyl ether of a cellulose film-forming organic polymer material which is not deteriorated by a neutral or alkaline aqueous medium, and from about 30% to about 80% by weight of the first coating layer of microcrystalline cellulose; and
   (c) a second coating layer amounting to between about 2% to about 10% by weight of the center, coating the first coating layer and consisting essentially of a microcrystalline cellulose-free pharmaceutically acceptable enteric organic polymer coating material selected from the group consisting of cellulose acetylphthalate, hydroxypropylmethylcellulose phthalate, benzophenyl salicylate, cellulose acetosuccinate, copolymers of styrene and of maleic acid, formylated gelatin, salol, keratin, stearic acid, myristic acid, gluten, acrylic and methacrylic resins, and copolymers of maleic acid and phthalic acid derivatives; each of said coating layers containing a plasticizer selected from the group consisting of diethylphthalate, dibutylphthalate, propylene glycol, caster oil and mixtures thereof.

2. A method of orally administering a pharmacologically active ingredient or a diagnostic agent for release in the colon, comprising the steps of orally administering a compressed tablet containing a pharmacologically active ingredient or a diagnostic agent to a subject having a colon needing treatment whereby said agent is not substantially released in the stomach or the small intestine and is practically entirely released in the colon, and wherein said compressed tablet is a tablet of claim 1.

3. The method of claim 2 wherein the active or diagnostic agent is barium sulphate.

4. The compressed tablet as defined in claim 1, wherein the film-forming material in the first coating layer is ethyl cellulose.

5. The compressed tablet as defined in claim 1, wherein the enteric coating material is cellulose acetylphthalate.

6. The compressed tablet as defined in claim 1 wherein the film-forming material of the first coating layer is ethyl cellulose, the enteric coating material is cellulose acetylphthalate and the plasticizer is selected from the group consisting of diethyl phthalate, dibutyl phthalate, propylene glycol, and mixtures thereof.

7. The method of claim 2 wherein the film-forming material in the first coating layer is ethyl cellulose, the enteric coating material is cellulose acetylphthalate and the plasticizer is selected from the group consisting of diethyl phthalate, dibutyl phthalate, propylene glycol and mixtures thereof.

* * * * *